(12) United States Patent
Wang et al.

(10) Patent No.: US 11,000,194 B2
(45) Date of Patent: May 11, 2021

(54) WRIST-WORN DEVICE AND BLOOD PRESSURE MEASURING METHOD BASED ON THE SAME

(71) Applicant: BOE TECHNOLOGY GROUP CO., LTD., Beijing (CN)

(72) Inventors: Zifeng Wang, Beijing (CN); Yan Ren, Beijing (CN); Lei Cao, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 187 days.

(21) Appl. No.: 16/316,259

(22) PCT Filed: Jan. 30, 2018

(86) PCT No.: PCT/CN2018/074582
§ 371 (c)(1),
(2) Date: Jan. 8, 2019

(87) PCT Pub. No.: WO2019/015294
PCT Pub. Date: Jan. 24, 2018

(65) Prior Publication Data
US 2020/0245876 A1     Aug. 6, 2020

(30) Foreign Application Priority Data
Jul. 21, 2017  (CN) .......................... 201710601906.2

(51) Int. Cl.
*A61B 5/021*     (2006.01)
*A61B 5/00*      (2006.01)
*A61B 5/318*     (2021.01)

(52) U.S. Cl.
CPC .......... *A61B 5/02141* (2013.01); *A61B 5/318* (2021.01); *A61B 5/681* (2013.01)

(58) Field of Classification Search
CPC combination set(s) only.
See application file for complete search history.

(56) References Cited

U.S. PATENT DOCUMENTS

2005/0177051 A1   8/2005  Almen
2011/0224529 A1*  9/2011  Lading ................... A61B 5/021
                                                    600/384
(Continued)

FOREIGN PATENT DOCUMENTS

CN          101884526 A    11/2010
CN          101708121 B     7/2012
(Continued)

OTHER PUBLICATIONS

Third Office Action for CN Application No. 201710601906.2, dated Nov. 18, 2019.
(Continued)

*Primary Examiner* — Paula J Stice
(74) *Attorney, Agent, or Firm* — The Webb Law Firm (57) ABSTRACT

A wrist-worn device and a blood pressure measuring method based on the same are disclosed. The wrist-worn device comprises a main body and a wrist band connected to the main body, and further comprises: a photoelectric tube located on a back surface of the main body and configured to collect pulse data of a wearer; electrodes configured to collect electrocardiograph data of the wearer, an insulator located between two of the electrodes, for preventing both from a direct electrical connection; a circuit board electrically connecting the photoelectric tube and the electrodes, the circuit board calculating a blood pressure value based on the collected pulse data and the electrocardiograph data.

9 Claims, 3 Drawing Sheets

(56) References Cited

U.S. PATENT DOCUMENTS

2017/0347895 A1* 12/2017 Wei ................... A61B 5/0537
2018/0301224 A1* 10/2018 Matichuk ............. A61B 5/4806

FOREIGN PATENT DOCUMENTS

| | | |
|---|---|---|
| CN | 204260741 U | 4/2015 |
| CN | 104622445 A | 5/2015 |
| CN | 204671169 U | 9/2015 |
| CN | 105411544 A | 3/2016 |
| CN | 205197986 U | 5/2016 |
| CN | 106236051 A | 12/2016 |
| CN | 106388809 A | 2/2017 |
| CN | 106419880 A | 2/2017 |
| CN | 106921763 A | 7/2017 |
| CN | 107233085 A | 10/2017 |
| EP | 1 468 645 A1 | 10/2004 |

OTHER PUBLICATIONS

First Office Action for CN Application No. 201710601906.2, dated Mar. 1, 2019.
International Search Report and Written Opinion for PCT/CN2018/074582 dated May 4, 2018.

* cited by examiner

WRIST-WORN DEVICE AND BLOOD PRESSURE MEASURING METHOD BASED ON THE SAME

CROSS REFERENCE TO RELATED APPLICATIONS

The present application is a U.S. National Stage under 35 U.S.C. § 371 of International Application No. PCT/CN2018/074582, as filed on Jan. 30, 2018, which claims priority to Chinese Patent Application No. 201710601906.2, as filed on Jul. 21, 2017, the disclosure of which is hereby incorporated by reference in its entirety.

TECHNICAL FIELD

The present disclosure relates to a wrist-worn device and a blood pressure measuring method based on the same.

BACKGROUND

The principle used in a related blood pressure measuring method is as follows: hardware is built with an undisturbed blood pressure detecting method based on a Photo Plethyamo Graph (PPG) signal and an electrocardiograph (ECG) signal, and then calibration is performed using the system algorithm before an Arterial Blood Pressure (ABP) value is output. In particular, a pulse signal is converted from a change in a diameter of the blood vessel of hands as detected by a photosensitive chip, the electrocardiograph signal is converted from a change in the capacitive difference between electrodes, and the built hardware platform may be a blood pressure measuring watch.

SUMMARY

A first aspect of the present disclosure provides a wrist-worn device, comprising a main body and a wrist band connected to the main body, further comprising: a photoelectric tube located on a back surface of the main body and configured to collect pulse data of a wearer; first, second and third electrodes configured to collect electrocardiograph data of the wearer, wherein the first electrode is located on the back surface of the main body; the second electrode is located at an edge of a front surface of the main body; the third electrode is located at a position of the edge of the front surface of the main body which is different from the position of the second electrode, or is located in a region on an inner side of the wrist band which contacts a skin of the wearer; an insulator located between the second electrode and the third electrode, for preventing both from a direct electrical connection; a circuit board electrically connecting the photoelectric tube and the three electrodes, the circuit board calculating a blood pressure value based on the collected pulse data and the electrocardiograph data.

Preferably, the second electrode and the third electrode are located at the edge of the front surface of the main body and are close to two connection parts of the main body and the wrist band, respectively.

Preferably, when the third electrode is located on an inner side of the wrist band, the third electrode comprises a plurality of metal sheets which are inlaid in the wrist band and exposed from an inner surface thereof, and wires serially connected among the metal sheets.

Preferably, when the third electrode is located on an inner side of the wrist band, the third electrode comprises a metal bar which is inlaid in the wrist band and exposed from an inner surface thereof.

Preferably, the photoelectric tube is located at a center of the back surface of the main body, and the first electrode is provided around the photoelectric tube.

Further, the insulator comprises an isolation part located between the second electrode and the circuit board for an electrical isolation therebetween, and the third electrode is connected to the circuit board by a wire which passes through the isolation part.

Further, the main body and the wrist band are connected and fixed by a metal thimble, and the metal thimble connects the third electrode within the wrist band and the wire within the insulator respectively, such that the third electrode is connected to the circuit board.

Preferably, the wrist-worn device further comprises: a battery located between a display screen of the main body and the circuit board for power supply, and a shield located between the circuit board and the battery.

Further, the wrist-worn device further comprises: a heat dissipation isolation layer located between the battery and the shield, the heat dissipation isolation layer leading out heat from the inside of the main body through the electrodes which are located at the edge of the front surface of the main body.

Correspondingly, a second aspect of the present disclosure further provides a blood pressure measuring method based on the wrist-worn device according to any one of the aforementioned technical solutions, comprising steps of:

contacting first, second and third electrodes with left and right arms respectively to form two loops so as to collect two sets of electrocardiograph data;

measuring pulse data of a wearer by a photoelectric tube;

calculating, by the circuit board, a blood pressure value, by processing the two sets of electrocardiograph data and a set of pulse data with an algorithm.

BRIEF DESCRIPTION OF THE DRAWINGS

In order to more clearly illustrate the technical solutions in the embodiments of the present disclosure, the drawings used in the description of the embodiments will be briefly described below. It is obvious that the drawings in the following description are only some embodiments of the present disclosure. Other drawings can also be obtained by those skilled in the art based on these drawings without paying any inventive effort.

DETAILED DESCRIPTION

In order to cause those skilled in the art to better understand solutions of the present disclosure, the technical solutions in the embodiments of the present disclosure will be clearly and completely described in the following with reference to the drawings in the embodiments of the present disclosure. Apparently, the described embodiments are only a portion of embodiments of the present disclosure, and not all of the embodiments. All other embodiments obtained by those skilled in the art based on the embodiments of the present disclosure without inventive efforts fall within the scope of the present disclosure.

In a blood pressure measuring watch in the related art, there is one electrode on a front surface of a main body, and there are two electrodes, as well as one photoelectric tube, on a back surface of the watch. During a procedure of the measurement, since the two electrodes on the back surface of the watch are convex, they contact the skin under a press of the other hand. In the whole procedure, the wrist on which the watch is worn easily sweats during an application of the press, which results in a short circuit of the two electrodes on the back surface of the watch and makes the measurement results inaccurate. Meanwhile, the contact manner between the two electrodes on the back surface of the watch and the arm results in discomfort, and a long-time hover of the pressing finger can also result in soreness and fatigue. Since stability of a metal state also significantly affects accuracy of the measurement, the aforementioned discomfort can also result in inaccuracy of the measurement results.

The present disclosure increases a contact area by distributing multiple (e.g. three) electrodes in a reasonable way so as to make the measurement results accurate and make the measurer feel comfortable throughout the measurement.

The first aspect of the present disclosure provides a wrist-worn device, comprising a main body, a wrist band connected to the main body, a photoelectric tube, first electrode, second electrode, third electrode, an insulator, and a circuit board.

The photoelectric tube is provided on a back surface of the main body and configured to collect s pulse data of a wearer. Preferably, the photoelectric tube may be provided at a center of the back surface of the main body.

The first, the second and the third electrodes are configured to collect electrocardiograph data of the wearer, wherein the first electrode is provided on the back surface of the main body, the second electrode is provided at an edge of a front surface of the main body, and the third electrode is provided at a position of the edge of the front surface of the main body which is different from the position of the second electrode, or is provided in a region on an inner side of the wrist band which contacts a skin of the wearer. Preferably, the first electrodes is provided around the photoelectric tube and occupies most area of the back surface of the main body. In particular, the "edge" in the edge of the front surface of the main body is directed to a region between the display screen and the outer sidewall of the main body.

The insulator is provided between the second electrode and the third electrode, and is configured to prevent both from a direct electrical connection.

The circuit board electrically connects the photoelectric tube and the first, the second and the third electrodes, and may calculate a blood pressure value based on the collected pulse data and the electrocardiograph data. The circuit board comprises contacts which are electrically connected to the first, the second and the third electrodes respectively. Preferably, the contacts comprise four contacts, and two contacts are provided on the front surface of the circuit board and two contacts are provided on the back surface of the circuit board, wherein two contacts on one surface are electrically connected to the first electrode, and two contacts on the other surface are electrically connected to the second electrode and the third electrode, respectively.

In order to facilitate a better understanding of the technical solutions of the present disclosure, several particular exemplary embodiments are listed specifically as follows.

Figure 1:
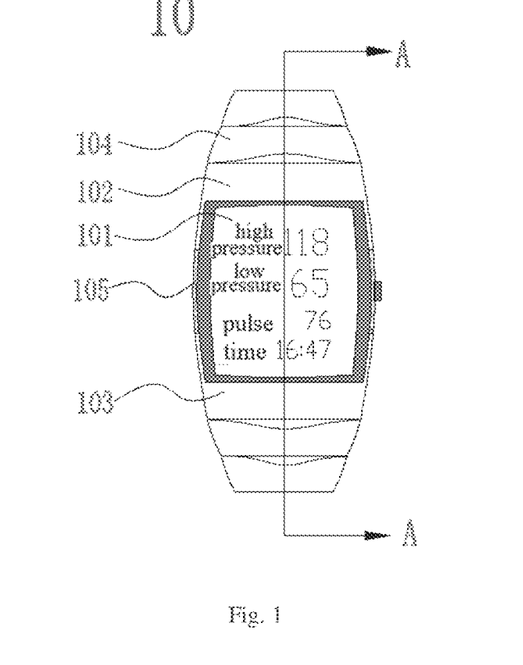
FIG. 1 is a structural schematic diagram of the wrist-worn device according to some embodiments of the present disclosure.
Figure 2:
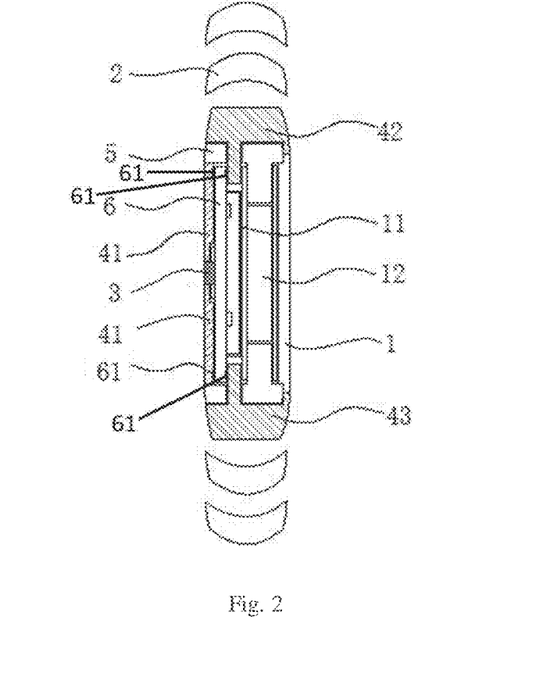
FIG. 2 is a cross-sectional view of the wrist-worn device as shown in FIG. 1 of the present disclosure in a direction of A-A'.

Referring to FIGS. 1 and 2, as a wrist-worn device 100 according to some embodiments, the second electrode 42 and the third electrode 43 are commonly provided at an edge of a front surface of the main body 1, and are close to two connection parts between the main body 1 and the wrist band 2, respectively.

In some embodiments, the second electrode 42 and the third electrode 43 may respectively face the two connection parts connecting the main body 1 and the wrist band 2, respectively occupy approximately one-half of the edge of the main body 1 in upper-lower symmetry, and are isolated by an insulator 5 therebetween. For example, when the main body 1 of the wrist-worn device 100 is rectangular, the second electrode 42 and the third electrode 43 divide the rectangular main body 1 into upper and lower symmetrical portions, and both are isolated by providing the insulator 5 therebetween. When the main body of the wrist-worn device is circular, the second electrode and the third electrode divide the circular main body into upper and lower approximate semicircles, and both are also isolated by providing the insulator therebetween. Positions of the second electrode 42 and the third electrode 43 may also refer to contact regions a and b in FIG. 6.

In other embodiments (not shown), the second electrode and the third electrode may be respectively close to the two connection parts connecting the main body and the wrist band, oppositely provided in a diagonal direction of the two connection parts, and isolated by the insulator therebetween. For example, when the main body of the wrist-worn device is a rectangle, the second electrode and the third electrode are respectively provided at two diagonal points of the rectangle, and both are isolated by providing an insulator therebetween.

In other embodiments (not shown), the second electrode and the third electrode may be provided on a same side of the diagonal direction of the connections, and both are isolated by the insulator and spaced from each other a certain distance so as to avoid a signal interference caused by a too short distance therebetween. For example, when the main body of the wrist-worn device is a rectangle, the second electrode and the third electrode are respectively provided at both ends of a same side of the rectangle, and both are isolated by providing an insulator therebetween.

In some embodiments, the back surface of the main body 1 may contact a skin of one wrist, and a photoelectric tube 3, which is packaged onto the circuit board 6 for measuring a human pulse, is provided at a center of the back surface of the main body 1. Four contacts 61 on both sides of the circuit board 6 contact the first electrode 41, the second electrode 42 and the third electrode 43, respectively, wherein the two contacts 61 contacting the first electrode 41 are internally conductive; the two contacts 61 contacting the second electrode 42 and the third electrode 43 respectively form two measuring loops, together with the two contacts 61 contacting the first electrode 41.

In some embodiments, the photoelectric tube 3 may be a reflective photoelectric sensor, of which a light-emitting tube (not shown) and a photosensitive receiving element (not shown) are commonly provided on the back surface of the main body 1. The photosensitive receiving element receives light which is emitted from the light-emitting tube and is reflected back by the blood, and measures the PPG signal. The specific principle is as follows: when a light beam of a certain wavelength irradiates onto a surface of a skin, the light beam will be transmitted to the photosensitive receiving element in a reflective way; during this procedure, the detected light intensity will be decreased due to absorption and attenuation effect of skin, muscle and blood at the detecting side, wherein the absorption of light by skin, muscle and tissue keeps constant throughout the blood circulation, a volume of blood within the skin shows a pulsatile change under an action of heart; when the heart is in systole, there is a maximum peripheral blood volume as well as a maximum light absorption amount, and thus a minimum light intensity is detected; when the heart is in diastole, conversely, a maximum light intensity is detected, and thus the light intensity as received by the photosensitive receiving element shows an impulsive change accordingly; a change in the volume pulse blood flow, namely a PPG signal, may be obtained by converting the light intensity change signal into an electrical signal.

In some embodiments, a battery 12 for power supply may be further provided between a 20 display screen of the main body 1 and the circuit board 6, and a shield 11 may be provided between the circuit board 6 and the battery 12, wherein the shield 11 may be provided on a chip-package side of the circuit board 6. Further, a heat dissipation isolation layer 1112 may be provided between the battery 12 and the shield 11, and the heat dissipation isolation layer 1112 can evenly distribute heat inside of the main body 1 and lead out the heat to the outside of the main body 1 through the second electrode 42 and the third electrode 43. Preferably, an adhesive layer is further provided between the battery 12 and the display screen.

In the embodiment of the present disclosure, three electrodes are taken as an example for illustrative description. However, those skilled in the art may understand, without deviating from spirit of the present disclosure, that more electrodes may be provided to measure electrocardiograph data.

Figure 3:
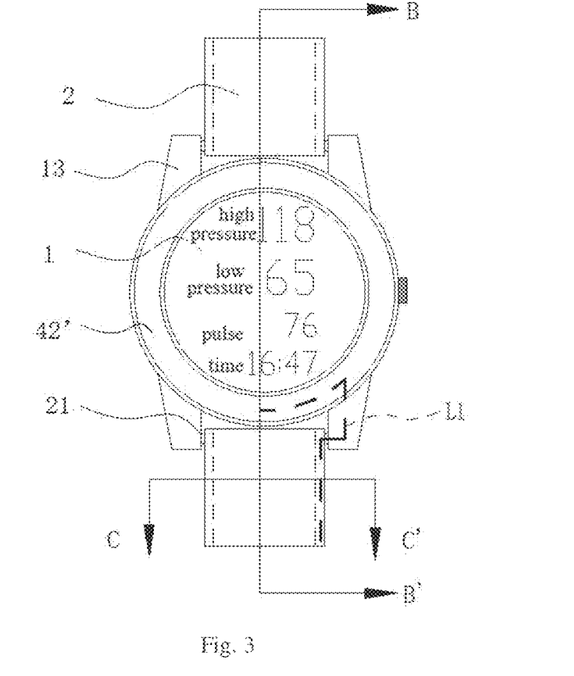
FIG. 3 is a structural schematic diagram of the wrist-worn device according to some other embodiments of the present disclosure.
Figure 4:
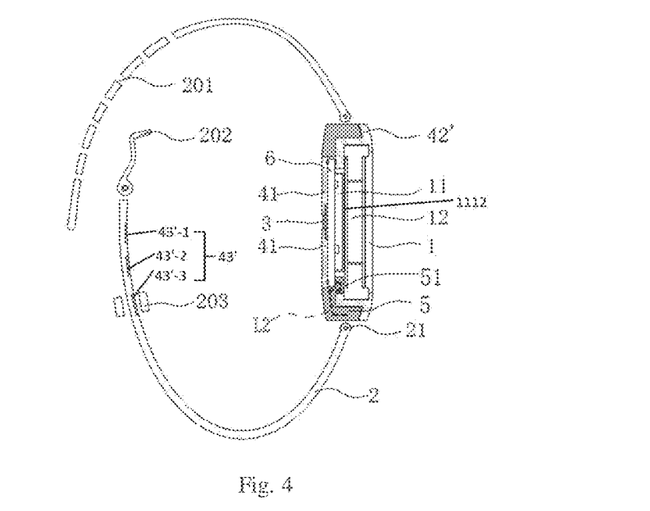
FIG. 4 is a cross-sectional view of the wrist-worn device as shown in FIG. 3 of the present disclosure in a direction of B-B'.
Figure 5:
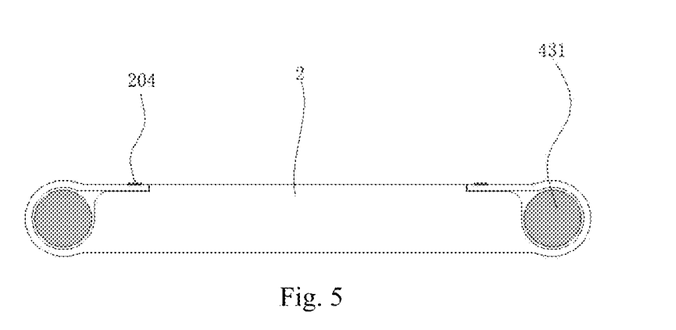
FIG. 5 is a cross-sectional view of the wrist-worn device as shown in FIG. 3 of the present disclosure in a direction of C-C'.

FIGS. 3 to 5 show a wrist-worn device 200 according to some other embodiments, which mainly differs from the wrist-worn device 100 according to the aforementioned some embodiments in the following: a different position at which the third electrode 43' is provided, and a different connection manner to the circuit board 6. Specifically, the third electrode 43' may be provided on an inner side of the wrist band 2; the main body 1 and the wrist band 2 may be connected and fixed by a metal thimble 21, and the metal thimble 21 are connected to the third electrode 43' within the wrist band 2 and the wire L2 within the insulator 5 respectively, such that the third electrode 43' is connected to the circuit board 6.

In some embodiments, the first electrode 41 may be provided around the photoelectric tube 3, and occupy most area of the back surface of the main body 1; the second electrode 42' is provided at an entire edge of the front surface of the main body 1; the third electrode 43' comprises a plurality of metal sheets 43'-1, 43'-2, and 43'-3 which are inlaid in the wrist band 2 and exposed from an inner surface thereof, and a wire L1 serially connected among the metal sheets 43'-1, 43'-2, and 43'-3, wherein the wire L1 may be a plurality of copper-axial thin wires 431 which are packaged at the edge of the wrist band 2. The main body 1 comprises an outer frame 13, within which the insulator 5 is provided, and the insulator 5 comprises an isolation part 51 located between the second electrode 42' and the circuit board 6 for an electrical isolation therebetween. The third electrode 43' is connected to the wire L2 which passes through the isolation part 51 by the metal thimble 21, and is finally connected to the circuit board 6. In some embodiments, the wrist band 2 may comprise watch buckle holes 201, a watch buckle 202, a watch buckle cover 203, and a suture 204 which packages the wrist band 2 (as shown by the dashed line portion on the wrist band 2 in FIG. 3); the metal sheets 43'-1, 43'-2, and 43'-3 are at least provided on the wrist band 2 at the watch buckle 202 end such that they may contact a skin of the wearer, but not provided at an end of the buckle hole 201 end, so as to avoid a noncontact with the skin of the wearer due to an overlap between the end of the buckle hole 201 end and the watch buckle 202 end during the wearing procedure.

In other embodiments (not shown), the third electrode may be further a metal bar which is inlaid in the wrist band and exposed from an inner surface thereof. The metal bar of the present embodiment requires no wire for connection in an extending direction of the wrist band. Preferably, the metal bar extends in a length direction of the wrist band, and may be a single bar which is provided at a position of the center line in an extending direction of the wrist band, or two bars which are provided on both sides of the center line in an extending direction of the wrist band, or a plurality of bars which are provided in parallel in an extending direction of the wrist band. In case of a plurality of bars, they may be connected to each other by wires. Also, both ends of the metal thimble are connected to the wire passing through the insulator and the metal bar provided within the wrist band respectively, such that the third electrode is connected to the circuit board.

It should be noted that, the wire L1 and the wire L2 may be two portions of the same wire which are located within the wrist band 2 and within the insulator 5 respectively, and thus their names are not distinguished.

Also, in some embodiments, a battery 12 for power supply may be further provided between the display screen of the main body 1 and the circuit board 6, and a shield 11 may be provided between the circuit board 6 and the battery 12, wherein the shield 11 is provided on the chip-package side of the circuit board 6. Further, a heat dissipation isolation layer 1112 is provided between the battery 12 and the shield 11, and the heat dissipation isolation layer 1112 may evenly distribute heat inside of the main body 1 and lead out the heat to the outside of the main body 1 through the second electrode 42'. An adhesive layer is further provided between the battery 12 and the display screen.

Further, the wrist-worn device 100, 200 may be integrated with some common functions of the wrist-worn device, for example, displaying a time or an electric quantity, and display them on the display screen on the front surface of the main body 1, in addition to the measurement of a blood pressure. In some embodiments, the wrist-worn device 100, 200 may have no display screen. The wrist-worn device 100, 200 may be connected to an electronic device such as a mobile phone, and output measurement data to the user on the display screen of the electronic device.

Correspondingly, some other embodiments of the present disclosure further provide a blood pressure measuring method based on the wrist-worn device according to any one of the aforementioned technical solutions, comprising steps of:

contacting first, second and third electrodes with left and right arms respectively to form two loops so as to collect two sets of electrocardiograph data;

measuring pulse data of a wearer by a photoelectric tube 3;

calculating, by the circuit board 6, a blood pressure value, by processing the two sets of electrocardiograph data and a set of pulse data with an algorithm.

In particular, the algorithm comprises a signal filtering process of the pulse data and the electrocardiograph data, the extracting of characteristic points, the calculating of a pulse transmit time PTT, and the building of a mathematical model for continuously measuring a blood pressure based on the PTT.

Figure 6:
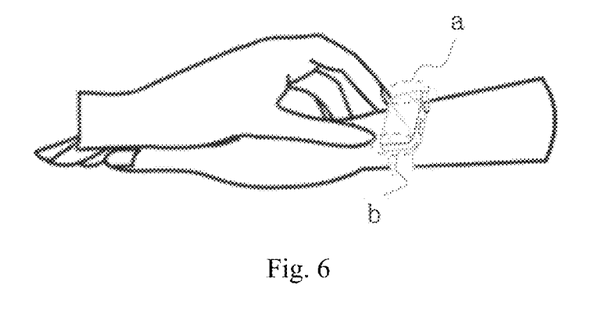
FIG. 6 is a schematic diagram of a blood pressure measurement based on the wrist-worn device according to some embodiments of the present disclosure.

In daily life, it is one of comfortable manners for a person to sit in front of a table in such a posture as to cross and superimpose first webs of both hands, which provides a basis of extension for the measuring method. Meanwhile when we use an ordinary watch and sometimes raises a wrist to look at the watch, a main body of the watch does not face us and needs to be righted by our hands. An ordinary righting position is at an edge around the watch. With reference to FIG. 6, a measuring method is shown in view of the usage habit of the watch and the comfort extent of the sitting posture for the aforementioned two points. That is, a palm of one hand of a user is superimposed on a back of the other hand, and the thumb and the forefinger of one hand are respectively placed at upper and lower edges of the watch on the other hand, namely contact regions a and b. In this way, the user will not feel uncomfortable even if the measurement lasts for a long time, and meanwhile it will also facilitate mental relaxation and stabilization of the measurement data.

Examples

A wrist-worn device 100 based on some embodiments may be that, the thumb and the forefinger of one hand are used to press two reference electrodes (a second electrode 42 and a third electrode 43) on the periphery of a front surface of the main body 1, such that a wrist of the other hand is attached to a first electrode 41 on a back surface of the main body 1 so as to form two measuring loops to measure two sets of electrocardiograph data of a human body, then a photoelectric tube 3 is used to measure pulse data on the wrist, and the three sets of data are processed by the circuit board 6 with a system algorithm before a blood pressure value of the human body is outputted and displayed on the display screen.

A wrist-worn device 200 based on some other embodiments may be that, the thumb and the forefinger of one hand are used to press the second electrode 42' on the periphery of a front surface of the main body 1, and one of two electrodes on the other hand is a first electrode 41 on a back surface of the main body 1 which is attached to the wrist, and the other one is a third electrode 43' serially connected in the wrist band 2 which is attached to the other side of the wrist. The three electrodes form two measuring loops to measure two sets of electrocardiograph data of a human body, then a photoelectric tube 3 is used to measure pulse data on the wrist, and the three sets of data are processed by the circuit board 6 with a system algorithm before a blood pressure value of the human body is outputted and displayed on the display screen.

As compared with the related art, the wrist-worn device according to the embodiments of the present disclosure has at least one or more of the following advantages.

(1) As compared with the related art in which two electrodes are commonly provided on a back surface of the main body, the present disclosure separately provides the first electrode on the back surface of the main body and provides the second electrode and the third electrode at an edge of the front surface of the main body, which increases a contact area of the electrodes, and places fingers of a measurer at a comfortable position during measurement, which facilitates the enhancement of stability of signal contact and thus facilitates the enhancement of accuracy of blood pressure measurement.

(2) The present disclosure provides a photoelectric tube at a center of the back surface of the main body, and separately provides the first electrode on the back surface of the main body and around the photoelectric tube, so as to guarantee accuracy of pulse measurement while causing the first electrode to have a contact area of a maximum range.

(3) The present disclosure provides the second electrode at an edge of the front surface of the main body, and provides the third electrode on the wrist band, which may be a metal bar extending in a same direction as the wrist band, which guarantees the two electrode to have a sufficient contact area and a stable contact between the third electrode and the arm, and facilitates the enhancement of accuracy of blood pressure measurement.

(4) The present disclosure provides the second electrode at an edge of the front surface of the main body, and provides the third electrode on the wrist band, which may be a plurality of metal sheets connected by a wire. On one aspect, a contact area of two electrodes is guaranteed, and on the other aspect, the electrodes is guaranteed to be not easily broken when the wrist band is bent during the wearing procedure. A good contact with the arm also facilitates accuracy of blood pressure measurement.

(5) The present disclosure provides a shield on the chip-package side of the circuit board, which may prevent the battery from interfering the magnetic field of the chip on the circuit board, guarantee stability of operation of the circuit, and also facilitate the enhancement of accuracy of blood pressure measurement.

(6) The present disclosure provides a heat dissipation isolation layer between the battery and the shield to evenly distribute heat inside of the main body and lead out the heat to the outside of the main body through the electrode at an edge of the main body, which solves the heating problem of operation of internal circuitry of the wrist-worn device and makes the operation thereof stable and the user wear comfortably.

An introduction is made for some embodiments provided by the present disclosure in detail above. For those skilled in the art, in accordance with ideas of the embodiments of the present disclosure, there are changes in the specific embodiments and application scopes. To sum up, the contents of this specification are not to be construed as limiting the present disclosure.

What is claimed is:

1. A wrist-worn device, comprising a main body and a wrist band connected to the main body, further comprising:
   an optical sensor provided on a back surface of the main body;
   a first electrode, a second electrode, and a third electrode, wherein the first electrode is provided on the back surface of the main body; the second electrode is provided at an edge of a front surface of the main body; the third electrode is provided at a position of the edge of the front surface of the main body which is different from the position of the second electrode, or is provided in a region on an inner side of the wrist band;
   an insulator located between the second electrode and the third electrode, for preventing the second electrode and the third electrode from a direct electrical connection; and a circuit board electrically connecting the optical sensor and the first, the second, and the third electrodes, wherein when the third electrode is located on the inner side of the wrist band, the third electrode comprises a plurality of metal sheets which are inlaid in the wrist band and exposed from an inner surface thereof, and a first wire serially connected among the plurality of metal sheets, wherein the first wire comprises a plurality of copper-axial thin wires which are packaged at an edge of the wrist band;

the insulator comprises an isolation part located between the second electrode and the circuit board for an electrical isolation therebetween, and the third electrode is connected to the circuit board by a second wire which passes through the isolation part; and the main body and the wrist band are connected and fixed by a metal thimble, and the metal thimble connects the third electrode within the wrist band and the wire within the insulator respectively, such that the third electrode is connected to the circuit board.

2. The wrist-worn device according to claim 1, wherein the second electrode and the third electrode are located at the edge of the front surface of the main body; and the second electrode and the third electrode are close to two connection regions where the main body and the wrist band are connected, respectively.

3. The wrist-worn device according to claim 2, wherein the circuit board comprises a first contact, a second contact, a third contact and a fourth contact, wherein the first contact and the second contact are provided on a first side of the circuit board, and the third contact and the fourth contact are provided on a second side of the circuit board;

the first contact and the second contact are contacted with the first electrode, and the first contact and the second contact are internally conductive;

the third contact is contacted with the second electrode, and the third contact forms a first measuring loop with the first contact and the second contact; and the fourth contact is contacted with the third electrode, and the fourth contact forms a second measuring loop with the first contact and the second contact.

4. The wrist-worn device according to claim 1, wherein the optical sensor is located at a center of the back surface of the main body, and the first electrode is provided around the optical sensor.

5. The wrist-worn device according to claim 1, further comprising: a battery located between a display screen of the main body and the circuit board for power supply, and a shield located between the circuit board and the battery.

6. The wrist-worn device according to claim 5, further comprising: a heat dissipation isolation layer located between the battery and the shield, the heat dissipation isolation layer leading out heat from the inside of the main body through the second and third electrodes which are located at the edge of the front surface of the main body.

7. The wrist-worn device according to claim 1, wherein the circuit board comprises a first contact, a second contact, a third contact and a fourth contact, wherein the first contact and the second contact are provided on a first side of the circuit board, and the third contact and the fourth contact are provided on a second side of the circuit board;

the first contact and the second contact are contacted with the first electrode, and the first contact and the second contact are internally conductive;

the third contact is contacted with the second electrode, and the third contact forms a first measuring loop with the first contact and the second contact; and the fourth contact is connected to the third electrode by the wire within the insulator, and the fourth contact forms a second measuring loop with the first contact and the second contact.

8. A blood pressure measuring method using a wrist-worn device, the wrist-worn device comprising a main body and a wrist band connected to the main body, the wrist-worn device further comprising: an optical sensor provided on a back surface of the main body and configured to collect pulse data of a wearer; a first electrode, a second electrode, and a third electrode, each of which is configured to collect electrocardiograph data of the wearer, wherein the first electrode is provided on the back surface of the main body; the second electrode is provided at an edge of a front surface of the main body; the third electrode is provided at a position of the edge of the front surface of the main body which is different from the position of the second electrode, or is provided in a region on an inner side of the wrist band which contacts a skin of the wearer; an insulator located between the second electrode and the third electrode, for preventing both from a direct electrical connection; and a circuit board electrically connecting the optical sensor and the first, the second, and the third electrodes, the circuit board calculating a blood pressure value based on the collected pulse data and the electrocardiograph data, wherein when the third electrode is located on the inner side of the wrist band, the third electrode comprises a plurality of metal sheets which are inlaid in the wrist band and exposed from an inner surface thereof, and a first wire serially connected among the plurality of metal sheets, wherein the first wire comprises a plurality of copper-axial thin wires which are packaged at an edge of the wrist band; the insulator comprises an isolation part located between the second electrode and the circuit board for an electrical isolation therebetween, and the third electrode is connected to the circuit board by a second wire which passes through the isolation part; and the main body and the wrist band are connected and fixed by a metal thimble, and the metal thimble connects the third electrode within the wrist band and the wire within the insulator respectively, such that the third electrode is connected to the circuit board, the blood pressure measuring method comprising steps of:

contacting the first electrode to one of a left or right arm and contacting the second electrode and the third electrode to the other of the left or right arm when the third electrode is provided at a position of the edge of the front surface of the main body which is different from the position of the second electrode, or contacting the first electrode and the third electrode to one of the left or right arm and contacting the second electrode to the other of the left or right arm when the third electrode is provided in a region on an inner side of the wrist band which contacts a skin of the wearer, to form two loops so as to collect two sets of electrocardiograph data;

measuring pulse data of the wearer by the optical sensor; and calculating, by the circuit board, a blood pressure value, by processing the two sets of electrocardiograph data and a set of pulse data with an algorithm.

9. The wrist-worn device according to claim 1, wherein the optical sensor collects pulse data;

the first, the second and the third electrodes collect electrocardiograph data; and the circuit board calculates a blood pressure value based on the collected pulse data and the electrocardiograph data.

* * * * *

UNITED STATES PATENT AND TRADEMARK OFFICE
CERTIFICATE OF CORRECTION

PATENT NO. : 11,000,194 B2  
APPLICATION NO. : 16/316259  
DATED : May 11, 2021  
INVENTOR(S) : Zifeng Wang et al.

Page 1 of 1

It is certified that error appears in the above-identified patent and that said Letters Patent is hereby corrected as shown below:

On the Title Page

Item [22], PCT Pub. Date, Line 1, delete "2018" and insert -- 2019 --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*